US008346703B2

(12) United States Patent
Gee et al.

(10) Patent No.: US 8,346,703 B2
(45) Date of Patent: Jan. 1, 2013

(54) SYSTEMS AND METHODS FOR ANALYZING COMMUNICATION OPTIONS

(75) Inventors: Robert Gee, Lake Barrington, IL (US); Edward Almquist, Bartlett, IL (US); Thomas Brey, Lake in the Hills, IL (US); Shafer Seymour, Bartlett, IL (US); Robert D'Avello, Lake Zurich, IL (US); Jonathan Lasch, Vernon Hills, IL (US)

(73) Assignee: Continental Automotive Systems, Inc., Auburn Hills, MI (US)

( * ) Notice: Subject to any disclaimer, the term of this patent is extended or adjusted under 35 U.S.C. 154(b) by 551 days.

(21) Appl. No.: 12/549,555

(22) Filed: Aug. 28, 2009

(65) Prior Publication Data
US 2011/0055133 A1   Mar. 3, 2011

(51) Int. Cl.
*G06N 5/02* (2006.01)

(52) U.S. Cl. .......................................................... 706/46
(58) Field of Classification Search ..................... 706/46; 340/902
See application file for complete search history.

(56) References Cited

U.S. PATENT DOCUMENTS

| 7,129,826 | B2 | 10/2006 | Nitz et al. | |
|---|---|---|---|---|
| 2005/0073432 | A1* | 4/2005 | Melman | 340/902 |
| 2005/0088318 | A1* | 4/2005 | Liu et al. | 340/902 |

\* cited by examiner

*Primary Examiner* — Jeffrey A Gaffin
*Assistant Examiner* — Ola Olude-Afolabi (57) ABSTRACT

Methods and systems for analyzing communication options, including determining one or more states of one or more communication-related conditions, and analyzing the one or more states and one or more communication options to determine an optimum communication option.

22 Claims, 5 Drawing Sheets

SYSTEMS AND METHODS FOR ANALYZING COMMUNICATION OPTIONS

I. BACKGROUND

The invention relates generally to the field of analyzing various communication options to determine one or more optimum communication options.

II. SUMMARY

In one respect, disclosed is a method for analyzing communication options, including: determining one or more states of one or more communication-related conditions; being provided with one or more communication options; and analyzing the one or more states and the one or more communication options to determine an optimum communication option.

In another respect, disclosed is a system for analyzing communication options, the system including: one or more processors; one or more memory units coupled to the one or more processors; one or more sensors coupled to the one or more processors, the sensors being configured to sense one or more states of one or more communication-related conditions; the system being configured to: be provided with one or more communication options; and analyze the one or more states and the one or more communication options to determine an optimum communication option.

In yet another respect, disclosed is a computer program product stored on a computer operable medium, the computer program product comprising software code being effective to analyze communication options by being effective to: determine one or more states of one or more communication-related conditions; be provided with one or more communication options; and analyze the one or more states and the one or more communication options to determine an optimum communication option.

Numerous additional embodiments are also possible.

III. BRIEF DESCRIPTION OF THE DRAWINGS

Other objects and advantages of the invention may become apparent upon reading the detailed description and upon reference to the accompanying drawings.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

IV. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

In some embodiments, systems and methods are disclosed for determining one or more optimum communication options. One or more states of one or more communication-related conditions are analyzed and, in response to analyzing the one or more communication-related conditions, one or more optimum communication options are determined. Communication options may include: calling using a cell phone, audible communications, communications using flashing lights, etc. In some embodiments, communication-related conditions may be any conditions that can influence the effectiveness of the various types of communication options.

In some embodiments, several other factors may be considered in determining the one or more optimum communication options or when and how often to use the one or more optimum communication options. Other such factors may include the amount of available power (in a vehicle, for example, this may include available fuel and battery power), health conditions of the one or more persons involved, other external conditions that may affect the health of the one or more persons involved, etc.

In some embodiments, the analysis of the communication options and the determination of one or more optimum communication options may be performed in a vehicle in response to an emergency, for example. In other embodiments, the analysis of the communication options may be performed in other transportation systems such as airplanes, boats, snow vehicles, submarines, etc. In yet other embodiments, aspects of the invention may be applied to situations that do not involve vehicles where the best communication option(s) may be required. It should be noted that the various embodiments presented here may be discussed in the context of vehicles and emergencies; however, the application of the invention should not be interpreted to be limited to those situations.

Location may be one of the communication-related conditions. Location may be used, for example, to determine whether the need for communication exists near a cell phone tower, near a populated area, near a hiking path, etc. Location information may be used in determining the optimum communication option, the direction in which to direct the communication, etc. Location information may also be used to obtain additional information using appropriate databases. For example, location information may be used to obtain weather information by looking up the weather information associated with that location in a weather database. Location information may also be used, for example, to determine situations in which certain communications options are not feasible/available, such as in a remote area where it is unlikely a person would be close enough to hear an audible signal, proximity to a large waterfall which might mask an audible signal, etc.

In some embodiments, location information may be obtained using satellite information such as GPS, Galileo, etc.

Location information may also be obtained, for example, using radio frequency triangulation techniques using one or more electromagnetic signals. Electromagnetic signals (even if 2-way communication is not possible) may include cellular tower signals, WiFi signals, FM/AM radio station signals, etc.

Vehicle location determination may also be performed or aided by map-matching, street sign recognition, and/or other object/landmark recognition (where the position of such objects may be known or estimated).

Vehicle location may also be determined using alternative reckoning techniques, such as dead reckoning. In some embodiments, the location of the vehicle may be determined using an initial known location, accelerometers, time, and equations of motions to calculate the current location.

Orientation of the vehicle may be another one of the communication-related conditions. The orientation of the vehicle may be used, for example, to determine in which direction to direct a particular type of communication, or to determine a probability of success for a particular type of communication, such as the probability of success of flashing the headlights given knowledge of an area where people may be present. Orientation information may also be used in combination with other data and databases to determine additional information. For example, knowledge of the vehicle's orientation combined with a topology database of the area may be used to determine an approximate location of the vehicle by comparing the vehicle's orientation to the slopes obtained from the topology databases to determine possible locations for the vehicle.

In some embodiments, the orientation of the vehicle may be obtained using a combination of accelerometers (g sensors) and compasses. A compass, for example, may be used to determine north-east-south-west orientation, and accelerometers may be used to determine the front-forward tilt and left-right tilt of the vehicle. In other embodiments, the orientation of the vehicle may be determined, approximately, using a vehicle's known location and a database of topology of the area.

Vehicle orientation may also be determined using dead reckoning techniques. For example, the orientation of the vehicle may be determined using an initial known orientation, accelerometers, and equations of motions to extrapolate a new orientation.

Date and time may be another of the communication-related conditions. Time may be used, for example, to determine whether it is day or night in order to determine whether flashing the lights would be a good way to signal for help. Time may also be used to determine whether other people or traffic may be in the vicinity. Date information may be used to determine average weather information such as temperature, rainfall, etc.

Weather information may be another of the communication-related conditions. Weather information may include rainfall, ambient light levels, electrical activity from lightning, audible activity from thunder, cloud cover, fog conditions, snow cover, ambient temperatures, etc.

Weather information may be used, for example, to determine whether to use flashing lights as means to communicate or whether to honk the horn as a means to communicate. For example, if the visibility is extremely low due to rain or fog, instead of flashing the lights, the horn may be used to attract attention. On the other hand, if communication is required during a very loud thunderstorm, the system may determine that honking the horn to attract attention would not be very effective. Predicted weather information over the next few hours/days may also be determined/obtained in order to determine optimum communication options for the next few hours/days.

In some embodiments, weather information may be determined using on-board sensors such as temperature sensors, rain sensors, humidity sensors, pressure sensors, audio sensors, light sensors, etc. In other embodiments, weather data may be received through weather broadcast. In yet other embodiments, weather data may be received over a data connection through the cellular network or a WiFi station, for example.

In some embodiments, weather information may also be estimated indirectly, such as through the use of the vehicle's traction control system to determine friction at the tires (suggesting rain/snow/ice) and also related temperature sensors (e.g., temperature <0 degrees C., and traction control indicating minimal friction/traction).

Ambient light information may be yet another one of the communication-related conditions. Ambient light information, in some embodiments, may be determined using one or more light sensors. In other embodiments, ambient light information may be determined using date and time information and a database that includes sunrise and sunset information, for example.

In some embodiments, ambient light information may be used to determine whether it is dark enough to use flashing lights, for example, as a means of communication. In other embodiments, ambient light may be used to determine lightning activity. In yet other embodiments, light sensors may be used to determine a direction of maximum light concentration at night in order to determine a direction in which to direct the one or more types of communication. In yet other embodiments, ambient light information may used to determine nearby traffic and perhaps the flow of that traffic to assist in the selection of which communication options to implement. In yet other embodiments, light sensors may be used to detect changes in light activity that may indicate nearby activity, such as a person or a vehicle walking or driving by.

Digital imaging information, including video and/or still image information, may be yet another one of the communication-related conditions. Digital imaging information, in some embodiments, may be obtained using one or more digital imaging cameras placed inside as well as outside of the vehicle.

In some embodiments, digital imaging of the surroundings may be used to determine the location of the vehicle. Nearby landmarks, signs, highway type (curvature, number of lanes, for example), etc, may be identified and an approximate location of the vehicle may be determined. Digital imaging information may also be used to determine orientation of the vehicle. For example, by viewing the orientation of a pole (known to be vertical) in the vicinity, orientation of the vehicle (tilt angle or angles) may be obtained as well as the direction in which the vehicle is facing. Digital imaging may also be used in determining weather conditions.

In some embodiments, digital imaging from inside the vehicle may be used to evaluate the health condition of the persons inside the vehicle. The information may be used, for example, to determine an amount of movement of each person in the vehicle. That information may be combined with other health-related information to determine the health status of the one or more persons inside the vehicle and accordingly appropriate communication options and frequency of those communication options.

Audio information may be yet another one of the communication-related conditions. Audio information, in some embodiments, may be obtained using one or more microphones placed inside and/or outside the vehicle. Such microphones may provide audio information via wire or wirelessly. External microphones may also be utilized in providing audio information to the vehicle, such as microphones from Bluetooth-connected phones.

In some embodiments, audio information may be used to supplement other information. For example, traffic sounds may used to verify the location of the vehicle. Directional microphones may be used to verify an orientation of the vehicle. Monitoring for outside sounds may be used to determine whether a person or persons are in the vicinity of the vehicle and thus where to direct communication attempts such as sounding the horn, flashing lights, etc. In other embodiments, audio information may also be used to detect the health condition of one or more persons involved by examining, for example, the sounds the persons may be making or not making after an accident.

Electromagnetic signal information may be yet another one of the communication-related conditions. Various spectrums of electromagnetic signals may be monitored for activity. In addition, the various spectrums may be compared to existing databases of such spectrums to obtain additional information.

In some embodiments, one or more antennas with corresponding tuners may be used to receive and process electromagnetic signal information. In some embodiments, simple antennas may be used; in other embodiments, directional antennas may be used configured to determine the direction as well as the intensity and frequency of specific signals. In other embodiments, specific signatures of electromagnetic signals as the signals are reflected from one or more buildings, hills, and other obstructions in the vicinity may be compared to an existing database of such signals to obtain additional information about the surroundings.

In some embodiments, changes to electromagnetic signals may be used to estimate material compositions of surrounding obstructions (estimating that these may be concrete, glass, steel, etc.), and those compositions may be compared with known database of obstructions (such as buildings on the west side of the road, for example) to determine location of the vehicle, etc.

In some embodiments, WiFi signals may be detected and compared to existing databases of WiFi signals. Triangulation techniques may then be implemented to determine an approximate location of the vehicle. Other spectrums may be similarly detected and utilized such as FM, AM, CB, WAAS, marine systems, aviation systems, etc.

In some embodiments, one or more spectrums may be monitored in order to determine whether activity exists in the vicinity, which could prompt the initiation of communications such as honking the horn, flashing the lights, etc. In other embodiments, communication bands may be monitored in order to determine channels having activity. Communication may be then initiated on those channels. For example, a conversation may be detected on a GPRS communication channel or data traffic might be detected on a local Wi-Fi network, which could prompt communication to be initiated on those channels.

Radar type information may be yet another one of the communication related conditions. In some embodiments, various frequencies of electromagnetic signals (including LIDAR or IR) and one or more transceivers may be used. In other embodiments, one or more sonar transceivers may also be used.

In some embodiments, radar may be used to determine one or more obstacles in the vicinity such as other vehicles, hills, buildings, etc. The information may then be used to determine an approximate location and/or orientation of the vehicle. In other embodiments, radar may also be used to monitor for activity in the vicinity, prompting communications that are directed in the direction of the activity. In yet other embodiments, the information detected using radar may be compared to existing databases in order to derive additional information. Radar information may also be used in order to determine whether the vehicle is in the vicinity of dangerous ground, such as a nearby cliff, for example.

Many other types of communication-related conditions may be sensed and monitored and be taken into account when determining one or more optimum communication conditions. Databases containing information of when and where construction workers may be working or when and where school children may be walking or when and where people activity may be present may be used. Other general information that may be used includes satellite location data, sun location data, moon location data, etc. Other general vehicle condition information obtained by vehicle systems may also be used such as accelerometer data from the on-board ESC/ABS systems, airbag data, vehicle and backup battery level and current consumption, engine status, rollover status, impact sensors and stored impact data, accelerometer data for ongoing movement, door locks, window status, sun/moon roof status, gas tank level, in-cabin temperature, seatbelt status, occupant sensors, etc.

In some embodiments, all the collected information may be used to determine one or more optimum communication options and the frequency with which to implement each of the one or more optimum communication options.

Information that may be combined may include available broadcast weather data, including barometric data if available, (in some embodiments, supplemented with on-board rain/water sensors), light levels, time of day, RADAR/LIDAR reflections (as may be caused by rain or fog or other obstructions), vehicle orientation, GPS/satellite signal strength (suggesting environmental conditions such as visibility), water conditions (as such conditions may cause hazardous driving conditions especially with a vehicle being off road or on a steep hill), potentially dangerous temperature shifts, etc.

In some embodiments, one or more communication options may be considered. Depending on available resources, one or more of these communication options may be used in parallel or in series to increase the likelihood that the communication will take place. The cellular network may be one communication medium. One or more cellular radios may be used to establish communication, for example. Other types of communication may include one or more satellite phones, one or more audio systems (such as vehicle's stereo system), one or more horns, lighting systems (such as a vehicle's headlights, turn signals, etc.), etc.

In some embodiments, one or more sensors and related devices may be used to detect the operability of the one or more available communication options. If a type of communication is inoperable, for example, that type of communication may not be considered in the process of determining the one or more optimum communication options. The operability of the headlights, for example, may be determined by a sensor that can measure the resistance of the bulbs. Alternatively, a combination of a light sensor and test electrical signals may be used to determine whether the headlights are operable. Similarly, the operability of the horn, for example, may be determined using appropriate sensors.

In some embodiments, after the states of the one or more communication-related conditions and one or more communication options are provided, an analysis is performed to determine one or more optimum communication options (and/or the frequency with which to apply the one or more of the optimum communication options). For example, a conditional probability of effectiveness may be determined according to some pre-defined algorithm for each of the communication options in order to determine which communication option to use. For each communication option, the one or more communication-related conditions may be considered according to their effect and state to determine a probability of successful communication for each of the available communication options. In some embodiments, the communication option(s) having the highest probability of success may be selected as the communication option.

In other embodiments, additional communication options may be considered and a combined probability may be constructed of the effectiveness of a combination and frequency of multiple communication options. For example, a sequence of one or more communication options having the highest probability of success may be considered and implemented.

In some embodiments, one or more power sources may be monitored to determine the total amount of available power. In some embodiments, the amount of available power may be one of the conditions that may be considered in determining one or more optimum communication options and/or the frequency with which to implement each of the one or more optimum communication options.

For example, probability functions may be constructed and used to predict the probability of successful communication of a sequence of communication attempts given the total amount of available power. A simple example of where the amount of available power may change the communication strategy may be: there is only enough power left to honk the horn twice for one minute in order to attract the attention of nearby people. If according to the information available to the system, students are supposed to walk by on their way to school in 5 hours and on their way back from school in 12 hours, the system will conserve and power and will not attempt to initiate communications at the moment. Instead, the system attempt communication using the horn in 5 hours for one minute and in 12 hours for another minute.

In some embodiments, the system may transfer power between the various systems as needed. For example, if there is available fuel but the battery in the vehicle is running low, the system may start the engine in order to charge the batteries. If other sources of power are available, such as solar panels, for example, the solar panels may be activated in order to charge the battery. Other power transfers may also be performed as needed.

In some embodiments, power conservation techniques may also be implemented to conserve power and extend the window of establishing successful communication. For example, the system may shut down systems that are consuming power and are no longer required, such as turning off headlights of vehicle after a vehicle has been in an accident or if the headlights are obstructed, cutting off power to devices in the vehicle that are inoperable and perhaps shorted out, turning off climate controls if the outside temperature does not require climate controls, etc.

In some embodiments, sensors may be used to determine the health status of the one or more persons involved. Examples of such sensors may include sensors embedded into the seats to detect breathing and heart rates, digital imaging sensors to detect general body movement and eye movement, audio sensors to detect human sounds, etc. In some embodiments, the detected information may also be supplemented with retrieved medical profiles for each of the one or more persons involved. The medical profiles may be stored locally or the profiles may be recovered over a data connection (the data connection may be to a local device or to a remote server). One or more identification methods may also be used to identify the one or more persons involved in order to retrieve, for example, the appropriate medical profile for each person.

In some embodiments, the health condition of the one or more persons involved may be another one of the conditions considered in determining the one or more optimum communication options. For example, if it is determined that there is a high probability that one or more of the persons involved is in critical health condition, a large amount of the available power may be dedicated to immediate and frequent attempts of communication in hope that communication may be established prior to a critical worsening in the person's health.

In some embodiments, one or more health-related conditions may be determined. Health-related conditions may be any conditions that can affect the health of the one or more persons involved. Examples of health-related conditions may include temperature inside the car, temperature outside the car, severe weather conditions, rising water level around the vehicle, presence of toxic gases, fuel leaks, short-circuits, fire, amount of available food and water, etc. In some embodiments, one or more sensors may be used to determine the health-related conditions, such as thermometers, water detectors, etc. The health-related conditions may be combined with other information and be considered in determining the one or more optimum communication options.

In addition, health-related conditions information may be combined with information on available power in order for the system to consider whether to use some of the available power to compensate for adverse health-related conditions. For example, if the system determines that it is dangerously cold outside and inside the cabin, the system may turn on the heater, especially in cases where the one or more persons in the vehicle are not conscious. Similarly, the system may roll up the windows if it is too cold/stormy/snowy outside, etc.).

In some embodiments, one or more optimum communication options may be determined by considering the states of the one or more communication-related conditions, the available communication options and their operability, the available power resources, the health condition of one or more persons involved, the states of one or more health-related conditions, etc.

For example, battery level, real-time current drain, availability of additional energy sources, environmental conditions (e.g., dangerously cold temperatures inside cabin and outside vehicle, or a vehicle that is sinking into the water), and availability of controls (which vehicle subsystems could be shut down or which ones are not responding yet draining power) may be used to adjust the communication strategy, while conserving power and perhaps diverting some power toward life-sustaining measures such as heating the seats or cabin.

Position information and additional sensors (such as light sensors, on-board clock, etc.) may be used to determine time-specific strategies for communication. For example, during the day, light flashing may not be deemed useful, but honking the horn may; during the night, flashing of lights that point toward a roadway may be combined with horn honking.

Sensors may be used to detect local movement in order to direct communication help requests toward the direction of local movement. For example, radar may be used to detect a person-sized object moving in front of the vehicle, triggering the flashing of the front lights and/or honking of the horn.

Detected crash-related information (in the event of a crash, for example) such as crash severity and direction, airbag deployments, seat belt status, etc. may be used to estimate potential medical needs of occupants. Accordingly, energy conservation may be balanced with immediate approaches for establishing communication while detecting potentially helpless occupants (e.g., by seat occupant sensors and/or the fact that seatbelt may be engaged after long periods of time) and using this information to determine life-sustaining strategies (e.g., not letting cabin temperature drop below a threshold temperature), etc.

Engine start (or other battery recharge mechanisms if available) may be initiated in order to recharge the vehicle's subsystems. In some embodiments, prior to starting the engine, collected and determined data (severity of crash, vehicle diagnostics, gas tank level changing slowly even though engine is off, overheat/fire sensors, position in grasslands or forest, etc.), may be used to determine whether it would be safe to start the engine. As a second step, available sensors may be monitored to determine if a problem is caused by the recharge strategy (camera detection of flames or smoke, sounds indicating problems such as explosions or cries of pain, etc.).

Active safety systems in a post-crash situation may be used to identify/classify targets and proximity for communication; that data may be used in life-saving measures to summon for help or to provide sustaining measures after the vehicle is no longer operative in its normal mode.

It should be noted that any and all of the above information may be supplemented by receiving input from one or more local persons and/or from one or more remote operators. For example, a person may input into the system what the person can see or hear from the vehicle. In addition, a remote operator in communication with the system may provide the system with additional information such as weather information, for example.

In some embodiments, a scoring (with weighted criteria) and ranking mechanisms may be used to determine the effectiveness of the different communication options. For example, for each potential communication option, weights may be assigned (with positive/negative indicators) showing the relative effect that each of a plurality of conditions may have on each communication option. In some embodiments, the "effectiveness scores" for each communication option may be normalized and ranked. This process may be repeated for different power consumption conditions (and other criteria such as the need for life-preserving measures as in the heating examples to avoid dangerously low temperatures), so that a decision as to which options to use could be made by combining the results of those various calculations, rankings, and absolute numbers (absolute numbers such as power consumption). In alternative embodiments, available power and life-preserving measures may be considered as part of the other conditions being considered.

Figure 1:
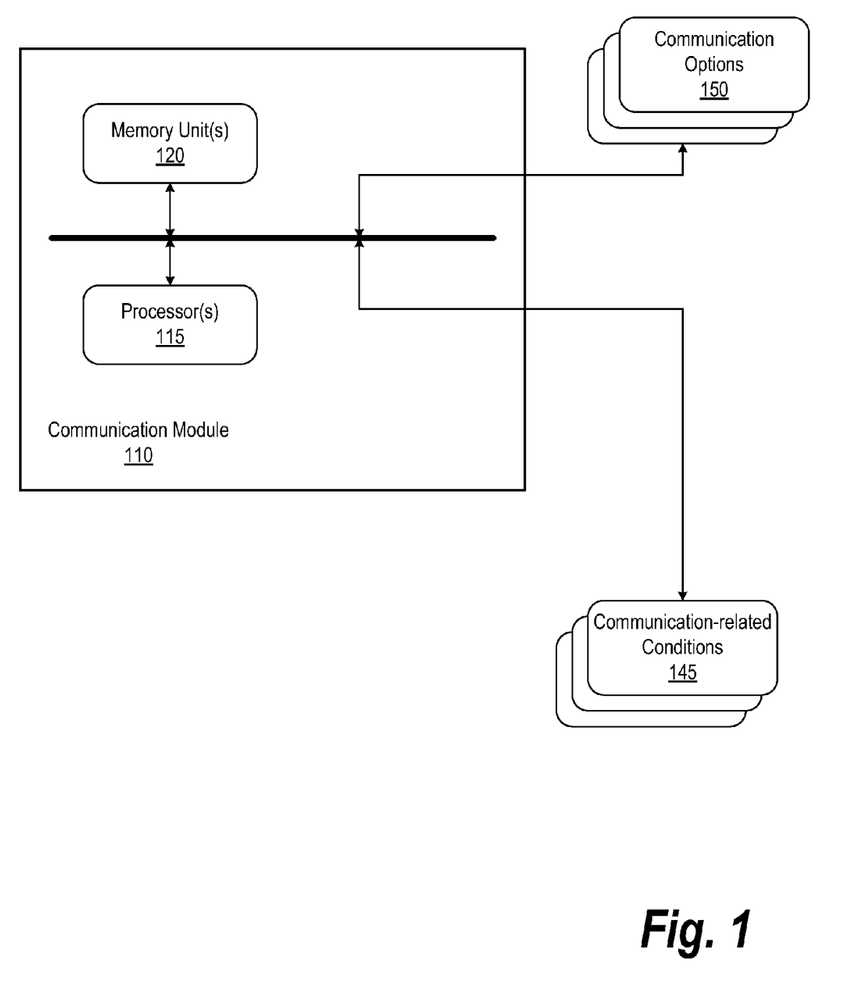
FIG. 1 is a block diagram illustrating a system for analyzing communication options, in accordance with some embodiments.

FIG. 1 is a block diagram illustrating a system for analyzing communication options, in accordance with some embodiments.

In some embodiments, communication module 110 is configured to determine an optimum communication method from one or more communication options such as one or more communication options 150. In some embodiments, communication module 110 may comprise one or more processors 115 and one or more memory units 120, which are coupled to one or more processors 115. Processors 115 and memory units 120 may be configured to perform the functionality of communication module 110. In other embodiments, other combinations of hardware units and/or software code may be used to implement communication module 110. The one or more communication options may include cellular radios, satellite phones, one or more audio systems (such as vehicle's stereo system), one or more horns, lighting systems (such as a vehicle's headlights, turn signals, etc.), etc.

Figure 2:
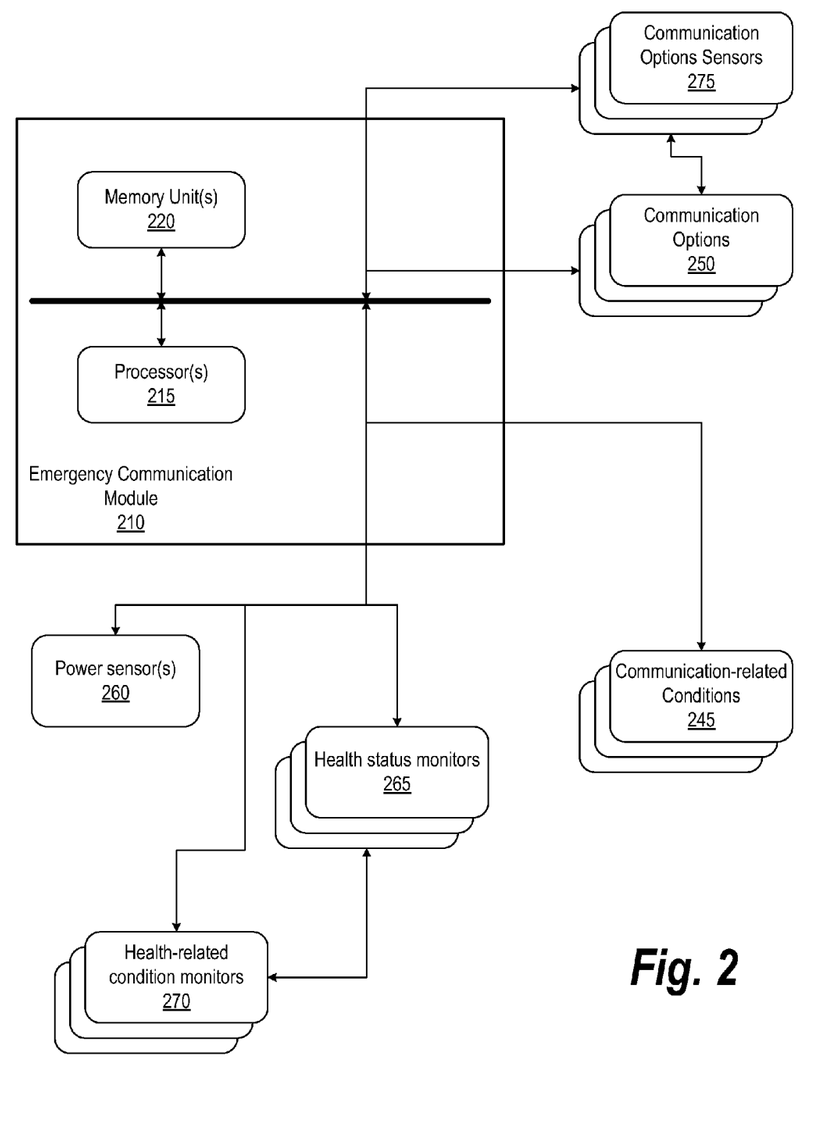
FIG. 2 is a block diagram illustrating an alternative system for analyzing communication options, in accordance with some embodiments.

In one embodiment, in order to determine an optimum communication option, the states of one or more communication-related conditions, such as communication-related conditions 145, may be analyzed. In some embodiments, communication-related conditions may include such conditions as location, orientation, data and time, weather, ambient light, digital imaging information, audio information, radio frequency information, radar, etc. In some embodiments, a probability function may be generated for each communication option, based on the analyzed communication-related conditions, in order to determine which communication option has the highest probability of being successful FIG. 2 is a block diagram illustrating an alternative system for analyzing communication options, in accordance with some embodiments.

In some embodiments, emergency communication module 210 is configured to determine an optimum communication method from one or more communication options such as one or more communication options 250. In some embodiments, emergency communication module 210 may comprise one or more processors 215 and one or more memory units 220, which are coupled to one or more processors 215. Processors 215 and memory units 220 may be configured to perform the functionality of emergency communication module 210. In other embodiments, other combinations of hardware units and/or software may be used to implement emergency communication module 210. The one or more emergency communication options may include cellular radios, satellite phones, one or more audio systems (such as vehicle's stereo system), one or more horns, lighting systems (such as a vehicle's headlights, turn signals, etc.), etc.

In one embodiment, in order to determine an optimum communication option, the states of one or more communication-related conditions, such as communication-related conditions 245, may be analyzed and weighted. In some embodiments, communication-related conditions may include such conditions as location, orientation, data and time, weather, ambient light, digital imaging information, audio information, radio frequency information, radar, etc. In some embodiments, a probability function may be generated for each communication option in order to determine which communication option has the highest probability of being successful.

In some embodiments, communication options sensors 275 are configured to determine the status of the one or more communication options 250. The status of the available communications options may be obtained in order to determine whether to consider one or more of the available communication options. For example, the status of the headlights (as a communication option) may be determined by measuring the resistance of the light bulb using a resistance sensor, for example, in order to decide whether to include the headlights in the list of available communication options. The status of other communication options may be similarly determined using other types of sensors, again in order to determine whether to consider the communication options.

In some embodiments, one or more power sensors 260 are configured to sense and report amounts of available power, such as amounts of fossil fuel, electrical power, etc. In some embodiments, the amount of available power may be one of the conditions to be considered when deciding on which communication option to implement and how often to attempt communication using that particular communication option. For example, there may be enough power to only honk the horn once in order to attract attention. Given this knowledge, the system may wait to use up the available power when there is a higher probability that a person that will hear the horn is in the vicinity.

In some embodiments, one or more health status monitors 265 are configured to sense the health conditions of one or more persons involved in the emergency. The health conditions being sensed may include heart rate, breathing rate, etc. Additional conditions may also be assessed such as general awareness of the one or more persons, whether the persons eyes are open, whether the persons are moving, whether and what type of sounds the persons may be making, etc. One or more of various types of sensors may be used to detect the health conditions, such as heart rate monitors, breathing sensors, digital imaging cameras, microphones, pressure sensors in the seats, occupant detection sensors, seat belt status changes (e.g., locked to unlocked), position of seat position controls, pressing of in-vehicle buttons, etc.

In some embodiments, health-related condition monitors 270 are configured to sense and determine one or more health-related conditions. Health-related conditions may be any conditions that may affect the health condition of the one or more persons involved directly or indirectly in the emergency. Health-related conditions may include temperature inside and outside the vehicle, humidity, fuel or energy source explosion probability, flooding probability, etc. In some embodiments, health-related condition information may be used in the process of determining an optimum communication option as one or more of the conditions. For example, the presence of extremely low temperatures may indicate to the system that it may be better to have frequent attempts of communication using different methods in hope for quick communication.

In some embodiments, emergency communication module 210 is configured to determine the frequency and type of optimum communication options based on: the one or more communication-related conditions; the one or more available communication options and their status; the available fuel and electrical power; the health conditions of one or more persons involved in the emergency; and the one or more states of one or more health-related conditions.

Figure 3:
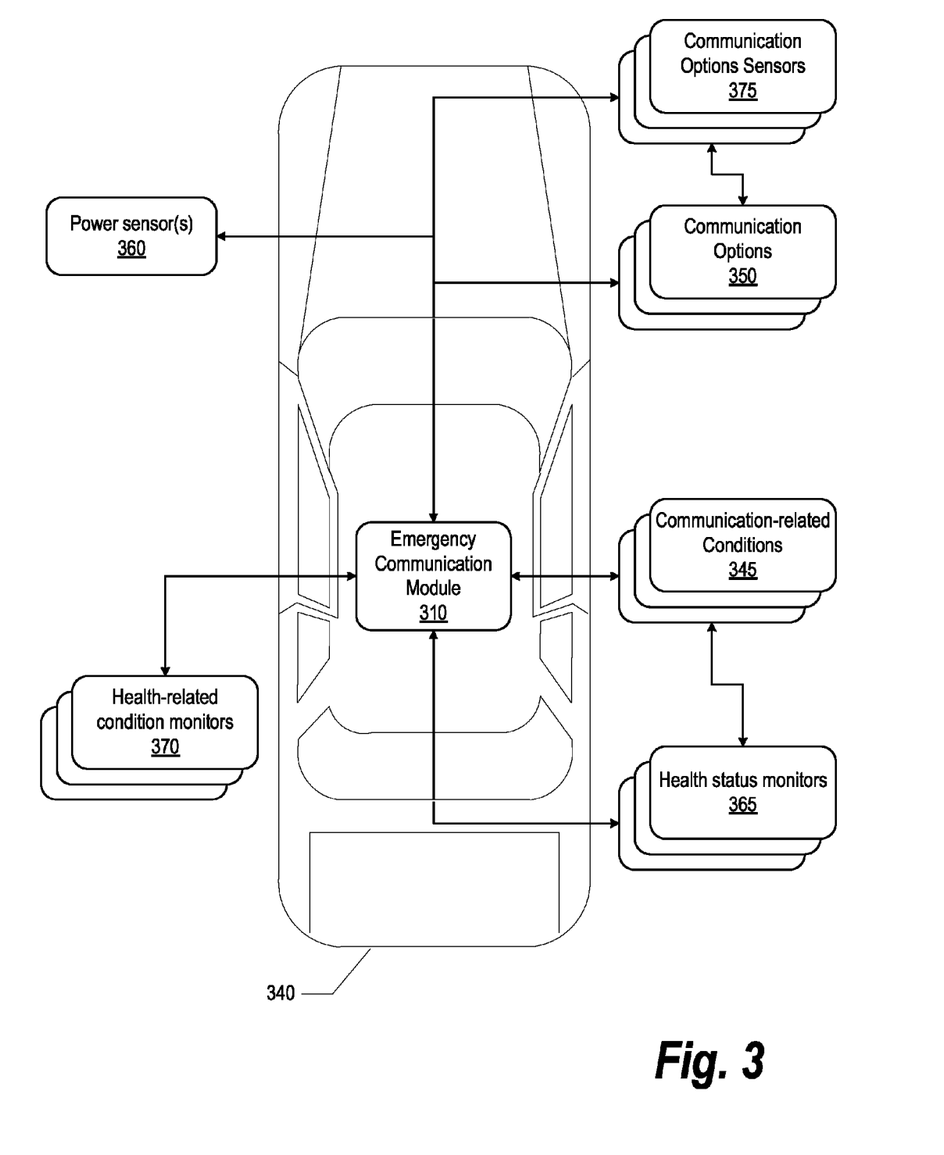
FIG. 3 is a block diagram illustrating a system for analyzing communication options as the system may be used in an automobile, in accordance with some embodiments.

FIG. 3 is a block diagram illustrating a system for analyzing communication options as the system may be used in an automobile, in accordance with some embodiments.

In some embodiments, vehicle 340 comprises emergency communication module 310, which is configured to determine an optimum communication method from one or more communication options such as one or more communication options 350. In some embodiments, emergency communication module 310 is configured to determine an optimum communication method in cases of emergency.

In some embodiments, emergency communication module 310 may comprise one or more processors and one or more memory units, which may be configured to perform the functionality of emergency communication module 310. In other embodiments, other combinations of hardware units and/or software may be used to implement emergency communication module 310. The one or more emergency communication options may include cellular radios, satellite phones, one or more audio systems (such as vehicle's stereo system), one or more horns, lighting systems (such as a vehicle's headlights, turn signals, etc.), etc.

In one embodiment, in order to determine an optimum communication option, the states of one or more communication-related conditions, such as communication-related conditions 345, may be analyzed and weighted. In some embodiments, communication-related conditions may include such conditions as location, orientation, data and time, weather, ambient light, digital imaging information, audio information, radio frequency information, radar, etc. In some embodiments, a probability function may be generated for each communication option in order to determine which communication option has the highest probability of being successful.

In some embodiments, communication options sensors 375 are configured to determine the status of the one or more communication options 350. The status of the available communications options may be determined in order to determine whether to consider one or more of the available communication options. For example, the status of the headlights may be determined by measuring the resistance of the light bulb using a resistance sensor, for example, in order to decide whether to include the headlights in the list of available communication options. The status of other communication options may be similarly determined using other types of sensors, again in order to determine whether to include the communication options in the list of available communication options.

In some embodiments, one or more power sensors 360 are configured to sense and report amounts of available power, such as amounts of fuel, electrical power, etc. In some embodiments, the amount of available power may be one of the conditions to be considered when deciding which communication option to implement and how often to attempt communication using that particular communication option. For example, there may be enough power to only honk the horn once in order to attract attention. Given this knowledge, the system may wait to use up the available power when there is a higher probability that a person that will hear the horn is in the vicinity.

In some embodiments, one or more health status monitors 365 are configured to sense the health conditions of one or more persons involved in the emergency. The health conditions being sensed may include heart rate, breathing rate, etc. Additional conditions may also be assessed such as general awareness of the one or more persons, whether the persons eyes are open, whether the persons are moving, whether and what type of sounds the persons may be making, etc. One or more of various types of sensors may be used to detect the health conditions, such as heart rate monitors, breathing sensors, digital imaging cameras, microphones, etc.

In some embodiments, health-related condition monitors 370 are configured to sense and determine one or more health-related conditions. Health-related conditions may be any conditions that may affect the health condition of the one or more persons involved directly or indirectly in the emergency. Health-related conditions may include temperature inside and outside the vehicle, humidity, fuel or energy source explosion probability, etc.

In some embodiments, emergency communication module 310 is configured to determine the frequency and type of optimum communication options based on: the one or more communication-related conditions; the one or more available communication options and their status; the available fuel and electrical power; the health conditions of one or more persons involved in the emergency; and the one or more states of one or more health-related conditions.

Figure 4:
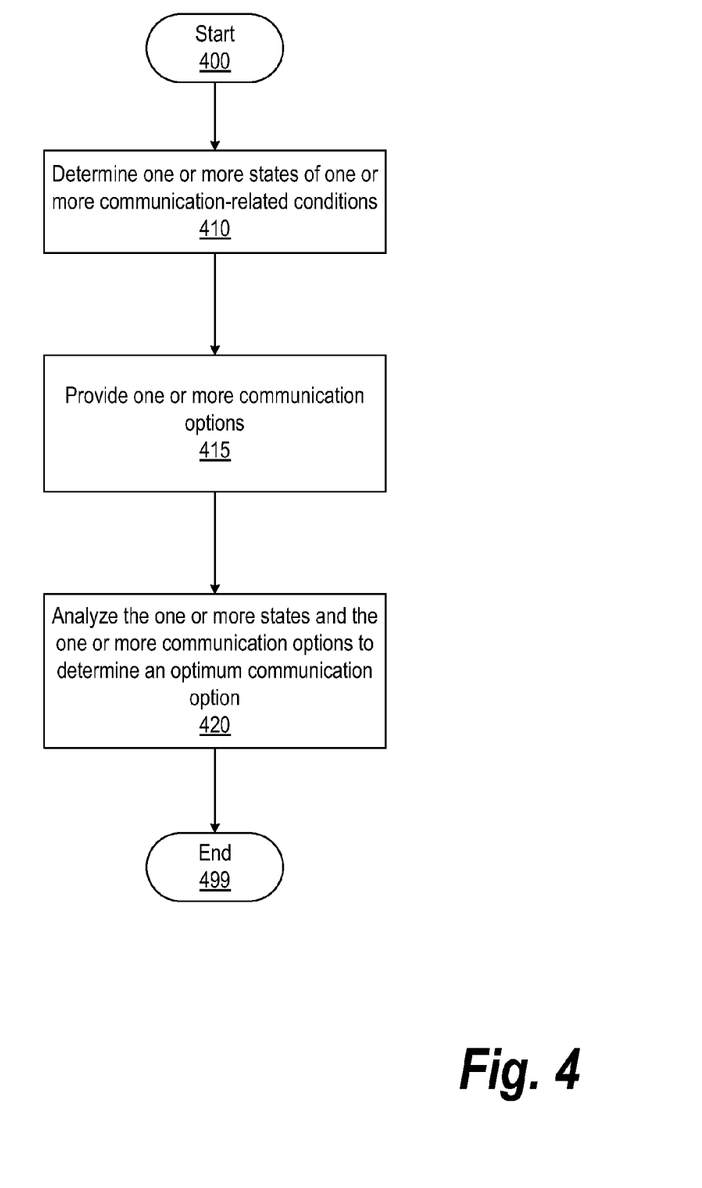
FIG. 4 is a flow diagram illustrating a method for analyzing communication options, in accordance with some embodiments.

FIG. 4 is a flow diagram illustrating a method for analyzing communication options, in accordance with some embodiments. In some embodiments, the methods described here may be implemented by a device such as the one described in FIG. 1 or FIG. 2.

Processing begins at 400 whereupon, at block 410, one or more states of one or more communication-related conditions are determined. In some embodiments, communication-related conditions may include such conditions as location, orientation, data and time, weather, ambient light, digital imaging information, audio information, radio frequency information, radar, etc.

At block 415, one or more communication options are provided. In some embodiments, communication options may include cellular radios, satellite phones, one or more audio systems (such as vehicle's stereo system), one or more horns, lighting systems (such as a vehicle's headlights, turn signals, etc.), etc.

At block 420, the one or more states of the one or more communication options are analyzed to determine an optimum communication option. In one embodiment, in order to determine an optimum communication option, the states of one or more communication-related conditions may be analyzed and weighted. In some embodiments, a probability function may be generated for each communication option in order to determine which communication option has the highest probability of establishing successful communication. In some embodiments, communication may be established in response to an emergency situation.

Processing subsequently ends at 499.

Figure 5:
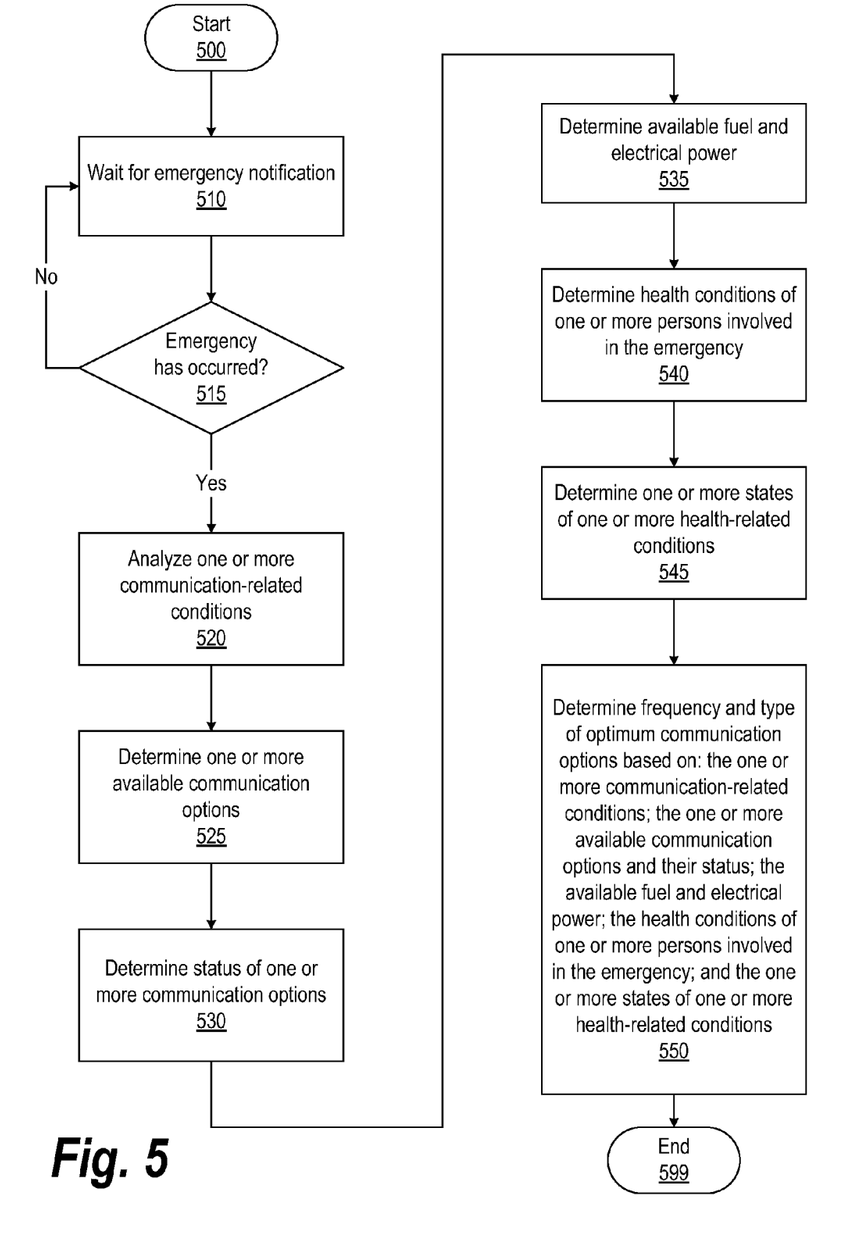
FIG. 5 is a flow diagram illustrating an alternative method for analyzing communication options, in accordance with some embodiments.

FIG. 5 is a flow diagram illustrating an alternative method for analyzing communication options, in accordance with some embodiments. In some embodiments, the methods described here may be implemented by a device such as the one described in FIG. 1 or FIG. 2.

Processing begins at 500, whereupon, at block 510, the system waits for emergency notification. In some embodiments, the system may be configured to determine (or even predict) when an emergency may occur. In other embodiments, emergency notification may be provided by one or persons identifying the emergency.

At decision 515, a determination is made as to whether an emergency has occurred. If an emergency has not occurred, decision 515 branches to the "no" branch and processing returns to block 510 where the system continues to wait for emergency notification. On the other hand, if an emergency has occurred, decision 515 branches to the "yes" branch where processing continues at block 520.

At block 520, one or more available communication-related conditions are analyzed. In some embodiments, communication-related conditions may include such conditions as location, orientation, data and time, weather, ambient light, digital imaging information, audio information, radio frequency information, radar, etc. Communication-related conditions may include any other condition that can have an effect on the one or more of the available communication options.

At block 525, one or more available communication options are determined. In some embodiments, communication options may include cellular radios, satellite phones, one or more audio systems (such as vehicle's stereo system), one or more horns, lighting systems (such as a vehicle's headlights, turn signals, etc.). Other available communication options may also exist.

At block 530, the status of the one or more available communication options are determined. The status of the available communications may be obtained in order to determine whether to consider one or more of the available communication options. For example, the status of the headlights may be determined by measuring the resistance of the light bulb in order to decide whether to include the headlights in the list of available communication options. The status of other communication options may be similarly determined, again in order to determine whether to include the communication options in the list of available communication options.

At block 535, available power, such as fuel and electrical power, are determined. In some embodiments, the amount of available power may be one condition to be considered when deciding which communication option to consider and how often to attempt communication using a particular option. For example, there may be enough power to only honk the horn once in order to attract attention. Given this knowledge, the system may wait to use up the available power when there is a higher probability that a person that will hear the horn is in the vicinity.

At block 540, the health conditions of one or more persons involved in the emergency are determined. The health conditions may include such things as heart rate and breathing rate. Additional conditions may also be assessed such as general awareness of the one or more persons, whether the persons eyes are open, whether the persons are moving, whether and what type of sounds the persons may be making, etc. One or more of various types of sensors may be used to detect the health conditions, such as heart rate monitors, breathing sensors, seat pressure sensors, digital imaging cameras, microphones, etc.

At block 545, one or more states of one or more health-related conditions are determined. Health-related conditions may be any conditions that may affect the health condition of the one or more persons involved directly or indirectly in the emergency. Health-related conditions may include temperature inside and outside the vehicle, humidity, fuel or energy source explosion probability, etc.

At block 550, frequency and type of optimum communication options are determined based on: the one or more communication-related conditions; the one or more available communication options and their status; the available fuel and electrical power; the health conditions of one or more persons involved in the emergency; and the one or more states of one or more health-related conditions.

Processing subsequently ends at 599.

Those of skill will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Those of skill in the art may implement the described functionality in varying ways for each particular application, but such implementation decisions should not be interpreted as causing a departure from the scope of the present invention.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A method comprising:
    analyzing a plurality of communication-related conditions selected from the group consisting of: location, orientation, date, time, weather, ambient light, digital-imaging information, audio information, radio frequency information, and radar information;
    determining availability of a plurality of communication options selected from the group consisting of: a cellular radio, a satellite telephone, an audio system, a horn, and a lighting system;
    determining a status condition for the available communication options;
    determining one or more types of optimum communication options based on: the plurality of communication-related conditions, the availability of communication options, and the corresponding status of available communication options.

2. The method of claim 1, wherein the step of analyzing communication related conditions comprises determining at least one of:
    a location, an orientation, a date and time, weather conditions, ambient light, digital image content, audio signals and radio frequency information.

3. The method of claim 1, further comprising the step of:
    communicating using at least two communications options at the same time to increase a likelihood that a communication will take place.

4. The method of claim 1, where the determining step further comprises determining an operability condition of a first communication option as being an optimum communication option and thereafter determining a second communication option as being an optimum communication option responsive to a determination that the first communication option is not available.

5. The method of claim 1, further comprising the steps of:
    determining at least one of: an amount of available electrical power and amount of fuel remaining; and
    selecting at least one communication option to use responsive to the step of determining at least one of: the amount of available electrical power and the amount of fuel remaining.

6. The method of claim 1, further comprising the steps of:
    determining one or more states of health related conditions of a person; and,
    selecting a communication option to use responsive to the step of determining one or more states of health related conditions of a person.

7. The method of claim 4, wherein the steps of determining an operability of a first communication system option as being an optimum communication option and thereafter determining a second communication option as option as being an optimum communication option responsive to a determination that the first communication option is not available is performed iteratively until all of the communication options have been determined as being optimum.

8. A system for analyzing communication options, the system comprising:
    one or more processors;
    one or more non-transitory memory units coupled to the one or more processors and storing program instructions executable by the one or more processors;
    one or more sensors coupled to the one or more processors, the sensors being configured to sense one or more states of one or more communication-related conditions;
    the system being configured to:
        analyze a plurality of communication-related conditions selected from the group consisting of location, orientation, date, time, weather, ambient light, digital-imaging information, audio information, radio frequency information, and radar information, the plurality of communication-related conditions being detectable by the one or more sensors;
        determine availability of a plurality of communication options selected from the group consisting of a cellular radio, a satellite telephone, an audio system, a horn, and a lighting system;
        determine a status condition for the available communication options;
        determine one or more types of optimum communication options based on: the plurality of communication-related conditions, the availability of communication options, and the corresponding status of available communication options.

9. The system of claim 8, being further configured to:
    analyze communication related conditions based on at least one of:
    a location, an orientation, a date and time, weather conditions, ambient light, digital image content, audio signals and radio frequency information.

10. The system of claim 8, where the system being configured to:
    communicate using at least two communications options at the same time to increase a likelihood that a communication will take place.

11. The system of claim 8, wherein the system is configured to determine an operability condition of the one or more communication options;
    and determine a second communication option to use an optimum communication option responsive to determining a first communication option is not available 12. The system of claim 8, being further configured to:
    determine at least one of an amount of available electrical power and amount of fuel remaining; and
    select at least one communication option to use responsive to the step of determining at least one of the amount of available electrical power and the amount of fuel remaining.

13. The system of claim 8, being further configured to determine:
    determine one or more states of health related conditions of a person; and,
    select a communication option to use responsive to the step of determining one or more states of health related conditions of a person.

14. The system of claim 11, wherein the steps of determining an operability of a first communication system option as being an optimum communication option and thereafter determining a second communication option as option as being an optimum communication option responsive to a determination that the first communication option is not available is performed iteratively until all of the communication options have been determined as being optimum.

15. The system of claim 8, further comprising a vehicle, the vehicle including the system for analyzing communication options.

16. A computer program product stored on a non-transitory computer operable medium, the computer program product comprising software code being effective to analyze communication options by being effective to:

analyze a plurality of communication-related conditions selected from the group consisting of: location, orientation, date, time, weather, ambient light, digital-imaging information, audio information, radio frequency information, and radar information determine availability of a plurality of communication options selected from the group consisting of: a cellular radio, a satellite telephone, an audio system, a horn, and a lighting system;

determine a status condition for the available communication options;

determine one or more types of optimum communication options based on: the plurality of communication-related conditions, the availability of communication options, and the corresponding status of available communication options.

17. The product of claim 16, the code being further configured to:

determine at least one of:

a location, an orientation, a date and time, weather conditions, ambient light, digital image content, audio signals and radio frequency information.

18. The product of claim 16, where the code being effective to:

communicate using at least two communications options at the same time to increase a likelihood that a communication will take place.

19. The product of claim 16, where the code being effective to determine an operability condition of the communication options and determine a second communication option to use as an optimum communication option responsive to determining a first communication option is not available.

20. The product of claim 16, where the code is further effective to:

determine at least one of: an amount of available electrical power and amount of fuel remaining; and selecting at least one communication option to use responsive to the step of determining at least one of: the amount of available electrical power and the amount of fuel remaining.

21. The product of claim 16, where the code is further effective to determine determine one or more states of health related conditions of a person; and, select a communication option to use responsive to the step of determining one or more states of health related conditions of a person.

22. The product of claim 19, wherein the step of determining a second communication option to use as an optimum communication option responsive to determining a first communication option is not available, is performed iteratively until all of the communication options have been determined as being optimum.

* * * * *